(12) United States Patent
Nikaido et al.

(10) Patent No.: US 8,414,929 B2  
(45) Date of Patent: Apr. 9, 2013

(54) MEDICAL SUBSTITUTE MEMBRANE, USE THEREOF, AND METHOD FOR REPAIR OF MEMBRANE TISSUE IN LIVING BODY

(75) Inventors: Toshio Nikaido, Toyama (JP); Motonori Okabe, Toyama (JP); Toshiko Yoshida, Toyama (JP); Shunro Endo, Toyama (JP); Nakamasa Hayashi, Toyama (JP); Shigeru Saito, Toyama (JP)

(73) Assignee: National University Corporation University of Toyama, Toyama (JP)

( * ) Notice: Subject to any disclaimer, the term of this patent is extended or adjusted under 35 U.S.C. 154(b) by 0 days.

(21) Appl. No.: 12/528,103

(22) PCT Filed: Feb. 21, 2008

(86) PCT No.: PCT/JP2008/052973

§ 371 (c)(1), (2), (4) Date: Aug. 21, 2009

(87) PCT Pub. No.: WO2008/102847

PCT Pub. Date: Aug. 28, 2008

(65) Prior Publication Data

US 2010/0098743 A1    Apr. 22, 2010

(30) Foreign Application Priority Data

Feb. 23, 2007 (JP) .................... 2007-043814

(51) Int. Cl.
- *A61F 2/00* (2006.01)
- *A61K 35/12* (2006.01)
- *A61K 35/54* (2006.01)
- *A01N 63/00* (2006.01)
- *A01N 65/00* (2009.01)

(52) U.S. Cl. ....... 424/582; 424/93.7; 424/423; 424/424; 424/520; 424/572

(58) Field of Classification Search .................. None  
See application file for complete search history.

(56) References Cited

U.S. PATENT DOCUMENTS

| 4,361,552 A * | 11/1982 | Baur, Jr. ................ 424/582 |
| 7,244,444 B2 * | 7/2007 | Bates ................... 424/423 |
| 2004/0126878 A1 * | 7/2004 | Ramos et al. ............ 435/366 |
| 2006/0153928 A1 * | 7/2006 | Kinoshita et al. ........ 424/582 |

FOREIGN PATENT DOCUMENTS

| JP | 63-260549 A | 10/1988 |
| JP | 8-266613 A | 10/1996 |
| JP | 10-113384 A | 5/1998 |
| WO | WO-2006/129673 A1 | 12/2006 |
| WO | WO-2007/023750 A1 | 3/2007 |

OTHER PUBLICATIONS

Von Versen-Hoynck, F. et al., "The influence of different preservation and sterilisation steps on the histological properties of amnion allografts—light and scanning electron microscopic studies", Cell and Tissue Banking, No. 5, pp. 45-56, (2004).

* cited by examiner

*Primary Examiner* — Debbie K Ware  
(74) *Attorney, Agent, or Firm* — Birch, Stewart, Kolasch & Birch, LLP

(57) ABSTRACT

The dried amniotic membrane is produced by drying a fresh amniotic membrane, which envelopes an embryo of an animal including human, and can be used as a substitute membrane for a membrane tissue in a living body; the dried amniotic membrane is dehydrated and dried so that the dried amniotic membrane can be stored in a dry air in a sterile state; when hydrated again by immersing in water or a buffer solution, the amniotic membrane still has an epithelial cell, a basement membrane and a connective tissue which constitute the fresh amniotic membrane. The dried amniotic membrane is useful as a medical substitute membrane for a membrane tissue in a living body such as a dura mater, a meninx, a pericardium, a pleura and a peritoneum.

6 Claims, 3 Drawing Sheets

FIG.3A
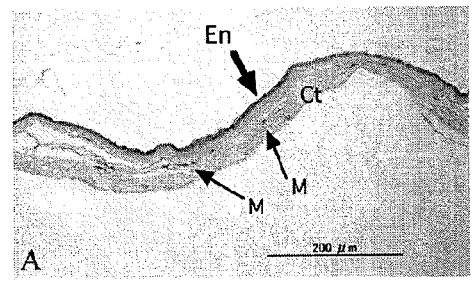
FIG.3B                    FIG.3C
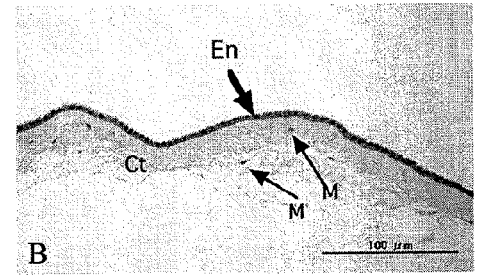    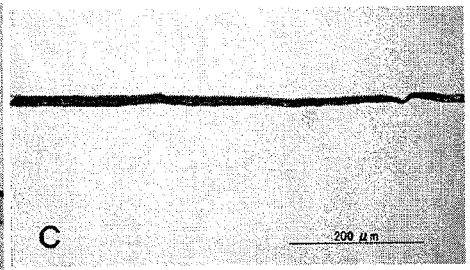
FIG.4A                    FIG.4B
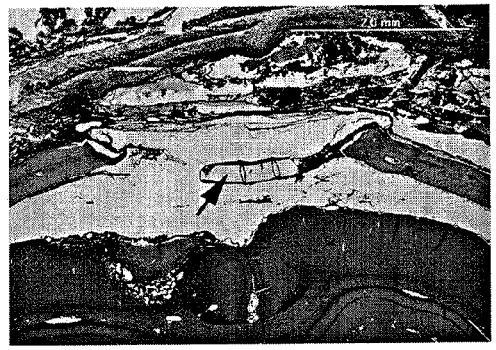    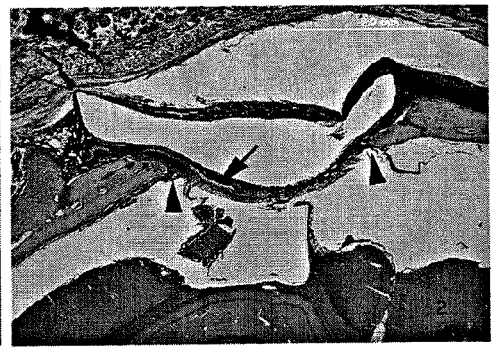
FIG.5
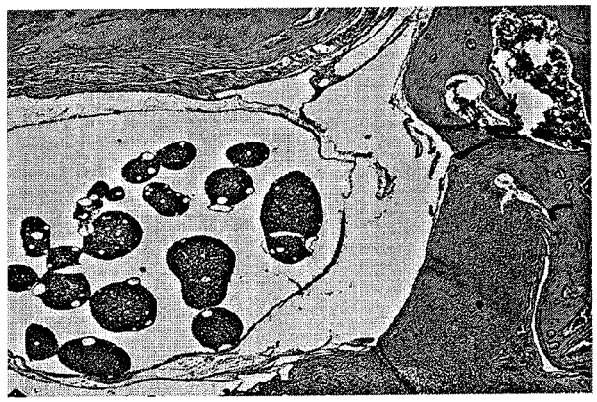

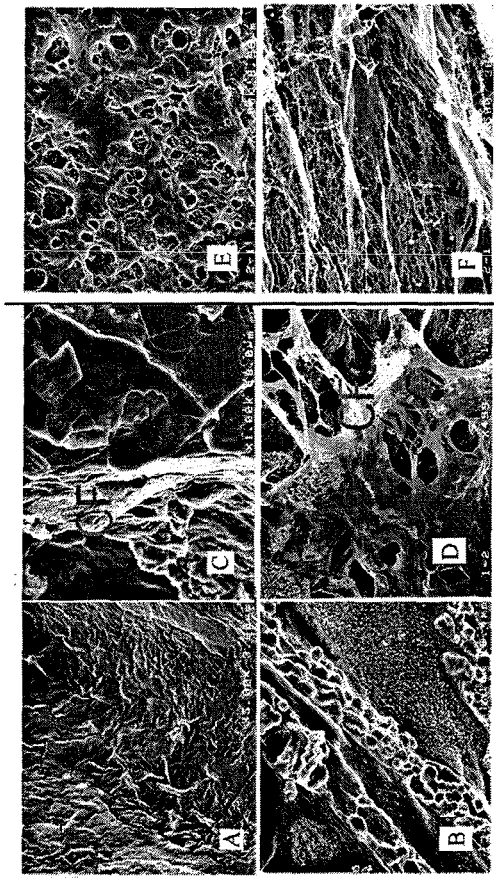

MEDICAL SUBSTITUTE MEMBRANE, USE THEREOF, AND METHOD FOR REPAIR OF MEMBRANE TISSUE IN LIVING BODY

CROSS-REFERENCE TO RELATED APPLICATIONS

The present application is a national phase under 35 U.S.C. §371 of PCT International Application No. PCT/JP2008/052973 which has an International filing date of Feb. 21, 2008, which claims priority of Application No. 2007-043814 filed in Japan on Feb. 23, 2007 under 35 U.S.C. §119.

FIELD

The present invention relates to a medical substitute membrane, a use of the medical substitute membrane and a method for repair of a membrane tissue in a living body, more precisely relates to a medical substitute membrane composed of a dried amniotic membrane, a use of the medical substitute membrane and a method for repair of a membrane tissue in a living body with using the medical substitute membrane.

BACKGROUND

A dura mater is an outermost membrane constituting a meninx between a skull and a brain, protects the brain and prevents leakage of a cerebral spinal fluid. The dura mater further covers a spinal cord to perform the similar functions. In a field of neurosurgery, various materials have been used for repairing dura maters.

For example, an allogenic graft of dura mater derived from human was a most-used material for repairing a dura mater. However, by using dura maters of human dead bodies, disease agents of Creutzfeldt-Jacob Disease (CDJ) were spread, so the use of human dura maters was significantly decreased. Further, there are following disadvantages: homology of the allogenic graft of dura mater derived from human is low; and provision thereof is limited.

Conventionally, a thigh muscle membrane from patient's own body and an artificial membrane composed of polytetrafluoroethlene and polyurethane polymer, e.g., Gore-Tex (registered trademark), have been used as a substitute film for a dura mater.

However, by using the artificial membrane, a chronic foreign-body reaction appears and handleability of the artificial membrane is low, so new biocompatible artificial membranes have been developed.

On the other hand, an amniotic membrane is a thin membrane part of placenta in uterus, which envelopes an embryo, and is disposed after birth of the baby.

An amniotic membrane has a basement membrane and no blood components, and it hardly causes rejecting reaction in case of being used for transplantation.

Further, an amniotic membrane reduces inflammatory reaction and accelerates repair of wounds, so it has been used, in a surgery field, to cover a burn injury part or to prevent organs from closing up after intraperitoneal surgery from a long time ago.

An amniotic membrane is a useful medical material capable of preventing fluid leakage and promoting the healing of wounds, so it is used as a prosthetic material of a urinary bladder, a urethra and a ureter (see Patent Document 1), as a medical material using a dense layer (collagen layer) of an amniotic membrane (see Patent Document 2) and as a substitute membrane, which is a layered body constituted by two collagen layers derived from an amniotic membrane and a sheet-shaped porous intermediate agent provided therebetween, for a cerebral dura mater, a pericardium, etc. (see Patent Document 3).

Patent Document 1: Japanese Patent Document No. P63-260549A
Patent Document 2: Japanese Patent Document No. P8-266613A
Patent Document 3: Japanese Patent Document No. P10-113384A

SUMMARY

As described above, amniotic membranes have been used as various medical materials. Therefore, the inventors think that amniotic membranes can be used as substitute membranes for a cerebral dura mater, a pericardium, etc.

In case of using an amniotic membrane as a substitute membrane for a cerebral dura mater, etc., it is most preferable to use an amniotic membrane enveloping an embryo of an animal including human, especially to use an amniotic membrane collected, in a sterile state, from human placenta by cesarean birth immediately after the collection.

However, a suitable amniotic membrane cannot be always obtained at the time of use, so fresh amniotic membranes, which have been previously obtained, must be stored.

Generally, a fresh amniotic membrane is soaked into a preservation fluid and frozen at temperature of −80° C. for reservation, and the frozen amniotic membrane is thawed at room temperature when it is used, but a preservation term of frozen amniotic membranes is about three months and the amniotic membranes will be incinerated when the term expires.

Further, when amniotic membranes are frozen, if water in cells of the amniotic membranes is frozen and large ice crystals are formed, the ice crystals will break cell membranes, so it is important to freeze amniotic membranes without forming large ice crystals, which break cells, in the cells and we have to pay particular attention to a cooling rate for freezing amniotic membranes.

In case of lyophilized amniotic membranes too, amniotic membrane tissues will be broken as well as the case of frozen amniotic membranes.

Namely, it is improper to use a dried amniotic membrane, whose cell membranes and amniotic membrane tissues have been broken, as a substitute membrane for a membrane tissue of a living body, e.g., cerebral dura mater.

Therefore, objects of the present invention are to provide a new medical substitute membrane for a living body, which is formed from a dried amniotic membrane and which is capable of solving the problem of the conventional lyophilized amniotic membrane used as a medical substitute membrane for a living body, i.e., breaking cell membranes and amniotic membrane tissues, to provide a use of the new medical substitute membrane, and to provide a method for repair of a membrane tissue in a living body.

The inventors have studied to solve the above described problem and found that a dried amniotic membrane, which is formed by storing and drying a fresh amniotic membrane enveloping an embryo of an animal including human, still has epithelial cells, a basement membrane and connective tissues constituting the fresh amniotic membrane when the amniotic membrane is rehydrated by immersing in water or a buffer solution.

Namely, the present invention is the medical substitute membrane being a dried amniotic membrane, the dried amniotic membrane being used as a substitute membrane in a living body and being produced by drying a fresh amniotic membrane, which envelopes an embryo of an animal including human, wherein the dried amniotic membrane is dehydrated and dried so as to store the dried amniotic membrane in a dry air in a sterile state, and the amniotic membrane still has an epithelial cell, a basement membrane and a connective tissue which constitute the fresh amniotic membrane when the amniotic membrane is rehydrated by immersing in water or a buffer solution.

And, the present invention is the use of a medical substitute membrane, said medical substitute membrane being a dried amniotic membrane, the dried amniotic membrane being used as a substitute membrane for a membrane tissue in a living body and being produced by drying a fresh amniotic membrane, which envelopes an embryo of an animal including human, wherein the dried amniotic membrane is dehydrated and dried so as to store the dried amniotic membrane in a dry air in a sterile state, and the amniotic membrane still has an epithelial cell, a basement membrane and a connective tissue which constitute the fresh amniotic membrane when the amniotic membrane is rehydrated by immersing in water or a buffer solution.

Further, the present invention is the method for repair of a membrane tissue in a living body being characterized by using a dried amniotic membrane as a medical substitute membrane, wherein the dried amniotic membrane is produced by drying a fresh amniotic membrane, which envelopes an embryo of an animal including human, the dried amniotic membrane is dehydrated and dried so as to store the dried amniotic membrane in a dry air in a sterile state, and the amniotic membrane still has an epithelial cell, a basement membrane and a connective tissue which constitute the fresh amniotic membrane when the amniotic membrane is rehydrated by immersing in water or a buffer solution.

In the present invention, the medical substitute membrane is suitably used as a substitute membrane for a dura mater.

EFFECTS OF THE INVENTION

The dried amniotic membrane used in the present invention can be easily treated without paying particular attention for preservation and conveyance.

Further, the amniotic membrane still has an epithelial cell, a basement membrane and a connective tissue which constitute the fresh amniotic membrane when the amniotic membrane is rehydrated by immersing in water or a buffer solution. Therefore, in case of using the dried amniotic membrane as a substitute membrane for a membrane tissue in a living body, the substitute membrane has equal effects with a fresh amniotic membrane.

BRIEF DESCRIPTION OF THE DRAWINGS

FIG. 3A shows an amniotic membrane rehydrated by immersing a dried amniotic membrane in a phosphate-buffered saline, and FIGS. 3B and 3C are optical micrographs of amniotic membranes rehydrated by immersing lyophilized amniotic membranes in a phosphoric acid buffer solution.

FIGS. 4A and 4B show tissue images of cerebral craniums of rats. An arrow in FIG. 4A indicates an artificial membrane composed of Gore-Tex (registered trademark).

FIG. 5 shows a tissue image of spinal cord of a rat.

DESCRIPTION OF EMBODIMENTS

Figure 1:
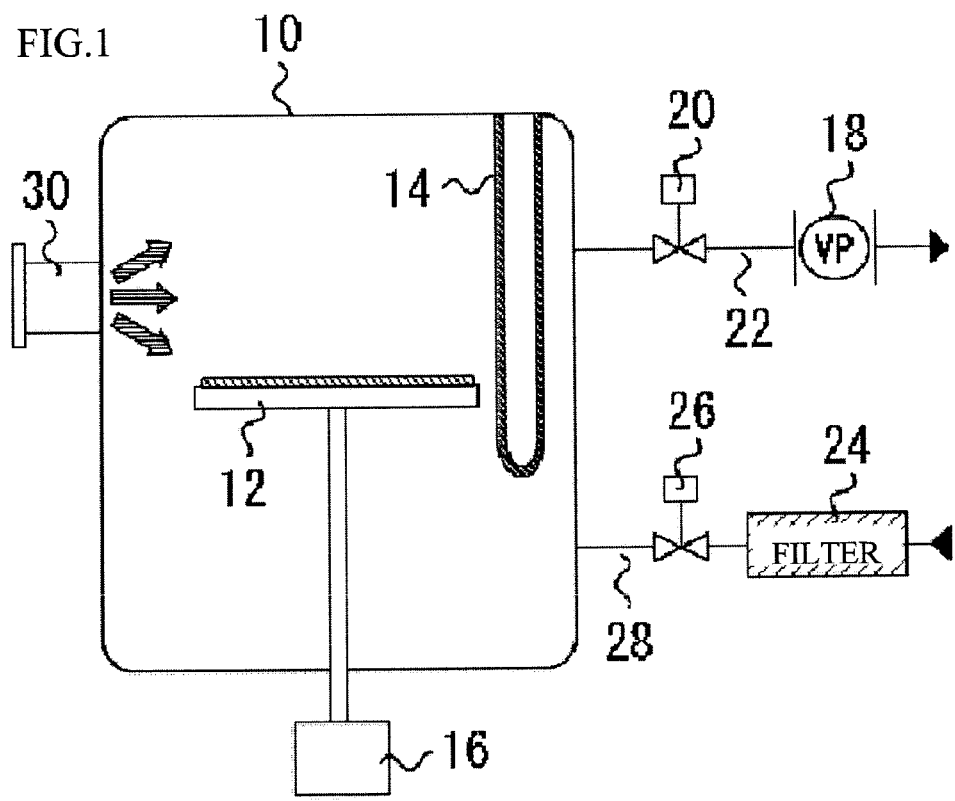
FIG. 1 is a schematic view of an example of a drying equipment for drying a fresh amniotic membrane.

A dried amniotic membrane used in the present invention can be produced by simultaneously irradiating a fresh amniotic membrane with a microwave and a far-infrared ray under reduced pressure.

For example, a drying equipment for drying a fresh amniotic membrane, which envelopes an embryo of an animal including human, includes: pressure-reducing means for reducing inner pressure of a processing tank, in which the fresh amniotic membrane has been set; heating means for heating the fresh amniotic membrane in the processing tank under reduced pressure; and pressure-increasing means for increasing the inner pressure of the processing tank to the atmospheric pressure, and the fresh amniotic membrane set in the processing tank is dehydrated and dried by the steps of: reducing the inner pressure of the processing tank, by the pressure-reducing means, with heating the fresh amniotic membrane, which has been set in the processing tank, by the heating means, so as to maintain temperature of the amniotic membrane at suitable temperature to prevent a basement membrane and connective tissues of the amniotic membrane from being broken; increasing the inner pressure of the processing tank to the atmospheric pressure; and alternately repeating the pressure-reducing step and the pressure-increasing step.

In the above described process of forming the dried amniotic membrane, at least one of a far-infrared ray heater and a microwave irradiator may be suitably used as the heating means. By setting temperature of the heating means at 50° C. or less, breakage of cell tissues can be highly prevented.

A fresh amniotic membrane derived from human can be suitably used as the fresh amniotic membrane to be dried, and the fresh amniotic membrane can be easily dehydrated by spreading the fresh amniotic membrane as a sheet of paper, in the processing tank.

When the inner pressure of the processing tank is increased to the atmospheric pressure, the inner pressure of the processing tank is made lower than the atmospheric pressure, so that the inner pressure of the processing tank can rapidly reach maximally reduced pressure by the next pressure-reducing step.

The dried amniotic membrane produced by the above described method (hereinafter merely referred to as "the dried amniotic membrane") can be stored for a long time by being sterilized and sealed in a sterile pack. Since cell tissues of the fresh amniotic membrane are substantially left, without being broken, in the dried amniotic membrane, an amniotic membrane similar to the fresh amniotic membrane can be produced by rehydrating the dried amniotic membrane in water or a buffer solution.

The dried amniotic membrane can be used as a medical substitute membrane for a membrane tissue in a living body such as a cerebral dura mater, a dura mater of a spinal cord, a meninx, a periosteum, a fascias, a pericardium, a pleura and a peritoneum.

By applying the dried amniotic membrane to an operative wound, a biologic membrane left around the operative wound, e.g., a dura mater, a meninx, a pericardium, a pleura, a peritoneum, extends or regenerates from a contact part, at which the biologic membrane is made contact with the dried amniotic membrane, by using the dried amniotic membrane as a scaffold, and the dried amniotic membrane will be decomposed and absorbed by a living body.

Further, the dried amniotic membrane can be used as a prosthetic material of a urinary bladder, a urethra and a ureter.

When the dried amniotic membrane is used as a substitute membrane, the dried amniotic membrane which has been cut into a suitable size may be adhered to cover a wound or implanted to fill a detective part. Further, the dried amniotic membrane may be hydrated in distilled water, physiological saline or a buffer solution before using.

The dried amniotic membrane which is strengthened by a chemical treatment with, for example, glutaric aldehyde may be used as a medical substitute membrane.

Further, the dried amniotic membrane in which a biocompatible sugar chain polymer or a medical agent is penetrated may be used as a medical substitute membrane.

First Embodiment (1) Collecting Fresh Amniotic Membrane

Consent was previously got from a pregnant woman and a placenta obtained from the woman, by cesarean birth, was immediately cleaned, in sterile physiological saline, to remove a chorionic membrane and blood coagulum, and then a fresh amniotic membrane was collected. The collected amniotic membrane was immediately sealed in a sterile spitz, together with physiological saline, and refrigerated.

(2) Drying Fresh Amniotic Membrane

The fresh amniotic membrane was dried by the drying equipment shown in FIG. 1. A magnetron having output power of 1.5 KW was used as a microwave irradiator 30 of the drying equipment. Preset temperature of a far-infrared ray heater 14 was 50° C., and the amniotic membrane was continuously irradiated with a far-infrared ray from the beginning of the dry process to the end thereof.

Further, maximally reduced pressure of a processing tank 10 controlled by a vacuum pump 18 was preset at 0.4 kPa while no amniotic membrane was set in the processing tank.

To dry the fresh amniotic membrane, 50 g of the fresh amniotic membrane, which had been taken out from the sterile spitz, was extended and put on a greaseproof sheet, whose both surfaces were coated with silicon resin, without forming creases, and then the extended fresh amniotic membrane was set on a tray together with the greaseproof sheet. Next, the tray was mounted on a turn table 12 in the processing tank 10, and then the turn table 12 was turned. The turn table 12 was continuously turned from the beginning of the dry process to the end thereof.

Then, the far-infrared heater 14 and the vacuum pump 18 were turned on, and an electromagnetic valve 20 was opened so as to start to reduce inner pressure of the processing tank 10. After a while, a pressure reduction rate was lowered, and then the vacuum pump 18 was turned off and the electromagnetic valve 20 was closed when the inner pressure reached the maximally reduced pressure of 0.90 kPa, further an electromagnetic valve 26 was opened so as to execute the pressure-increasing step, in which air from which dusts and bacteria were removed by a filter 24 was introduced into the processing tank 10, until the inner pressure of the processing tank 10 reached 4.53 kPa. When the pressure-increasing step was started, the magnetron used as the microwave irradiator 30 was turned on to irradiate the amniotic membrane on the turn table 12 with a microwave so as to heat the amniotic membrane.

Both of the far-infrared ray heater 14 and the magnetron heated the amniotic membrane for three minutes, and then the magnetron was turned off and the pressure-reducing step was started again with the far-infrared ray heater 14 being turned on. The inner pressure of the processing tank 10 was reduced until reaching 0.62 kPa, and then the inner pressure of the processing tank 10 was increased again until reaching 4.63 kPa and the amniotic membrane was heated, by the far-infrared ray heater 14 and the magnetron, for three minutes. The pressure-reducing step, the heating step and the pressure-increasing step were repeated six times until completing the dry process. The completion of the dry process was determined on the basis of the maximally reduced pressure of the processing tank 10 of the fifth pressure-reducing step and the maximally reduced pressure of the processing tank 10 in which no amniotic membrane was set. Namely, the maximally reduced pressure of the processing tank 10 of the sixth time reached 0.40 kPa and was made equal to that of the processing tank 10 in which no amniotic membrane, so that the completion of the dry process could be determined.

The fresh amniotic membrane set in the processing tank 10 was 50 g; the weight of the dried amniotic membrane which had been dehydrated and dried was 1 g, and the dried amniotic membrane was sealed in a sterile pack for preservation.

(3) Condition of Dried Amniotic Membrane

Figure 2A:
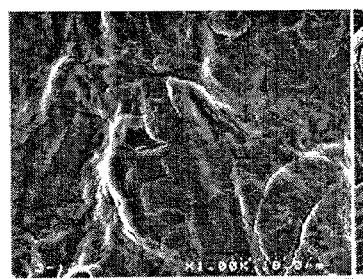
FIGS. 2A-2C show scanning electron micrographs of surfaces of a dried amniotic membrane.
Figure 2B:
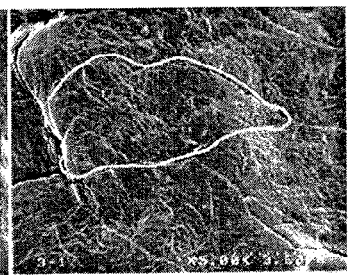
Figure 2C:
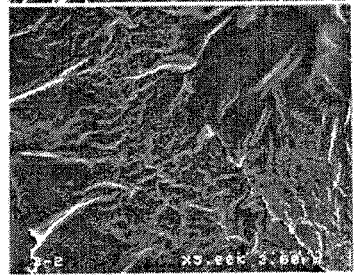

By observing both surfaces of the dried amniotic membrane with a scanning electron microscope, the dried amniotic membrane had a certain structure, which was flat with less undulation and breakage, as shown in FIGS. 2A-2C. FIGS. 2A-2C are scanning electron micrographs of different parts of the surface of the dried amniotic membrane, and they show the flat certain structure with less undulation and breakage. In FIG. 2B, it is thought that a part enclosed by a line is one of cells, and the cells like fish scales are seen.

Note that, in FIGS. 2A and 2C which show the opposite surface of the surface shown in FIG. 2B, no clear structure is observed, so it is thought that connective tissues existing under epithelium which includes ground substance are securely maintained.

A specimen of the amniotic membrane, which had been rehydrated by immersing in a phosphate-buffered saline, was formed by an ordinary manner of producing a microscopic specimen and was observed by an optical microscope, so that an epithelial cell (En), a connecting tissue (Ct) and messenchymal cells (arrows M) were observed as shown in FIG. 3A, as well as the fresh amniotic membrane shown in FIG. 3B.

A micrograph of another specimen of an amniotic membrane, which was formed by rehydrating a lyophilized amniotic membrane in a phosphate-buffered saline, is shown in FIG. 3C just for reference. The lyophilized amniotic membrane significantly atrophied, and epithelial cells (En) and connecting tissues (Ct) were not observed.

(4) Applying Dried Amniotic Membrane to Periosteum

Each of rats was anesthetized by pentobarbital intraperitoneal injection and locked in an abdominal position, and then skin of a temporal part was cut and opened to expose a temporal skull bone, further a periosteum of 1 cm square was exposed by an electric drill.

A dura mater was removed, and then the dried amniotic membrane was put on a defective part, from which the dura mater had been removed. A bone defective part was filled with bone wax, and then the skin was sutured. On the other hand, in a control group, an artificial membrane, e.g., Gore-Tex (registered trademark), was used instead of the dried amniotic membrane.

Change of the wounds with the passage of time was observed. After two weeks, a rat was anesthetized by using pentobarbital and was fixed by perfusion method using formalin. A head was cut, a decalcification treatment was performed, and then the cut sample was embedded to study characteristics of the transplanted amniotic membrane by a morphological method. Another treated rat lived for three months or more, and no inflammation was observed at the treated part.

(5) Histogenetical Change

In a control group, tissue connection between the broken skull bones was not observed after four weeks, and connective tissues slightly extended from periosteums were observed. Void caused by leaking a cerebral spinal fluid from a cranial cavity (storage of an eosinophilic substance and existence of cell debris were observed in the vacuoles) were formed in head skin of the part where a cerebral cranium had been removed, and cellular infiltration was extensively observed. Further, grafts of the control groups were left without change (see FIG. 4A).

In the group of using the dried amniotic membranes, cells grew from a periosteum of a cerebral cranium with using the amniotic membrane as a support medium, and the separated bone ends were connected so that the cranial cavity could be closed and separated from outside.

Therefore, structures of a dermis and a subcutaneous tissue were kept normal as well as a non-surgical damaged place, where was not operated. The tissues extended from the periosteum broke into skin of scalp and a skull, and formed vacuoles, but storage of an eosinophilic substance and existence of cell debris were not observed (see FIG. 4B).

Further, thin ossein was observed under the grown cell layer on the cranial cavity side.

Second Embodiment (1) Applying Dried Amniotic Membrane to Dura Mater

Each of rats was anesthetized by pentobarbital intraperitoneal injection and locked in an abdominal position, and then skin of a thoracolumbar part was cut and opened to expose a vertebral body. Further, a part of an vertebral arch was removed, by an electric drill, to expose a dura mater. A part of the dura mater of 1 cm square was removed, and then the dried amniotic membrane, which had been produced by the method of Example 1, was put on a defective part, from which the dura mater had been removed. Muscle and subcutaneous tissues were sutured without treating the bone defective part. On the other hand, in a control group, an artificial membrane, e.g., Gore-Tex (registered trademark), was used instead of the dried amniotic membrane.

Change of the wounds with the time course was observed. After two weeks, a rat was anesthetized by using pentobarbital and was fixed by perfusion method using formalin. The defective part, on which the amniotic membrane had been put, was cut together with the adjacent vertebral body. Next, a decalcification procedure was performed, and then the cut sample was embedded to study characteristics of the transplanted amniotic membrane by a morphological method.

(2) Histogenetical Change

In both of the group of using the dried amniotic membranes and a control group, a difference of external characteristics between the groups was not observed. In the group of using the dried amniotic membranes, connection between the amniotic membrane and a periosteum was observed as shown in FIG. 5. Further, bone regeneration on the amniotic membrane was observed, and the amniotic membrane had characteristics of an original dura mater of a spinal cord.

Field Of Industrial Application

The dried amniotic membrane of the present invention is useful as a medical substitute membrane for a membrane tissue in a living body such as a dura mater, a meninx, a pericardium, a pleura and a peritoneum.

What is claimed is:

1. A method for repair of a membrane tissue in a living body, comprising:
    a step of setting a fresh amniotic membrane, which envelopes an embryo of an animal, in a processing tank;
    a step of drying the fresh amniotic membrane by a heating means while reducing an inner pressure of the processing tank to produce a dry amniotic membrane that still has an epithelial cell, a basement membrane, and a connective tissue; and
    a step of repairing a membrane tissue of a wound area of the living body, in which the dry amniotic membrane is put on, embedded into, or fills the wound area;
    wherein the dry amniotic membrane is used to repair a dura mater of the living body.

2. The method according to claim 1,
    wherein a process of reducing the inner pressure of the processing tank and a process of increasing the inner pressure until reaching the atmospheric pressure are alternately repeated in said drying step.

3. The method according to claim 1,
    wherein the heating means used in said drying step is at least one of a far-infrared ray heater and a microwave irradiator.

4. The method according to claim 1, wherein the fresh amniotic membrane is heated at a temperature of 50° C. or lower in said drying step.

5. The method according to claim 1,
    wherein the dry amniotic membrane is rehydrated by immersing in water or a buffer solution, and the rehydrated amniotic membrane is put on, embedded into, or fills the wound area so as to repair the membrane tissue of the wound area.

6. The method according to claim 1, wherein the animal is a human.

\* \* \* \* \*

UNITED STATES PATENT AND TRADEMARK OFFICE
CERTIFICATE OF CORRECTION

| | | |
|---|---|---|
| PATENT NO. | : 8,414,929 B2 | Page 1 of 1 |
| APPLICATION NO. | : 12/528103 | |
| DATED | : April 9, 2013 | |
| INVENTOR(S) | : Toshio Nikaido et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Second Day of July, 2013

Teresa Stanek Rea
*Acting Director of the United States Patent and Trademark Office*